(12) United States Patent
Desai

(10) Patent No.: US 6,461,296 B1
(45) Date of Patent: Oct. 8, 2002

(54) METHOD AND APPARATUS FOR DELIVERY OF GENES, ENZYMES AND BIOLOGICAL AGENTS TO TISSUE CELLS

(75) Inventor: Ashvin H. Desai, San Jose, CA (US)

(73) Assignee: 2000 InjecTx, Inc., San Jose, CA (US)

( * ) Notice: Subject to any disclaimer, the term of this patent is extended or adjusted under 35 U.S.C. 154(b) by 0 days.

(21) Appl. No.: 09/510,537

(22) Filed: Feb. 22, 2000

Related U.S. Application Data

(63) Continuation-in-part of application No. 09/105,896, filed on Jun. 26, 1998, now Pat. No. 6,231,591.

(51) Int. Cl.[7] .............................................. A61B 1/32
(52) U.S. Cl. ...................................... 600/210; 604/105
(58) Field of Search ............................ 604/8, 105, 110, 604/113; 600/210, 225

(56) References Cited

U.S. PATENT DOCUMENTS

| | | | |
|---|---|---|---|
| 4,854,302 A | * 8/1989 | Allred | 128/6 |
| 5,073,166 A | * 12/1991 | Parks | 604/105 |
| 5,122,122 A | * 6/1992 | Allgood | 604/105 |
| 5,613,950 A | * 3/1997 | Yoon | 604/105 |

* cited by examiner

Primary Examiner—Michael A. Brown
(74) Attorney, Agent, or Firm—David Jaffer; Pillsbury Winthrop LLP

(57) ABSTRACT

A method and apparatus for delivery of genes, enzymes and biological agents to tissue cells, including a method and apparatus wherein treatment fluids, including genes, enzymes and biological agents, are injected into a target area of a body providing selective attachment to the specific target cells without affecting normal tissue cells. The method is used to treat prostate cancer, breast cancer, uterine cancer, bladder cancer, stomach, lung, colon, and brain cancer, etc. A hollow core needle is inserted into a body, the needle being visually guided by a selected imaging technique. A first embodiment utilizes an endoscopic instrument, wherein a probe is inserted into the body, guided by the endoscope to the vicinity of the target area. The hollow core needle is guided to the vicinity by a channel through the probe. A needle adjustment apparatus is used to extend or retract the needle and adjust needle tip orientation toward a target area. The endoscope provides a view to an operator for adjustment of the apparatus to extend the tip of the needle into and through tissue, interstitially, to a target area for deposit of the specific treatment fluid. A non-invasive imaging technique is used either alone, or in addition to the endoscope, to give an operator a view of the needle for guiding the needle tip to the precise target area. Typical non-invasive techniques include CT scan, MRI, ultrasound, etc.

12 Claims, 13 Drawing Sheets

THERAPY FLUIDS

- Necrossing Agents
    - Ethanol Alcohol (1% to 100% Pure)
    - Saline Solution (0.9% to 99%)
    - Acetic Acid (1% to 100%)
    - Natural Extracts/Compounds
    - Enzymes

- Anesthetic Agents
    - Lidocaine
    - Markaine
    - Sensorcaine

- Antibiotics

- Genes

- Virus

- Vaccines

- Proteins

- Tumor Suppression Genes

- Inhibitors

- Tissue Markers

- Other Biological Agents

- Bioabsorbable Polymers

- Polymers with Chemotherapeutic Agents and Pharmaceutical Drugs

- Contrast Agents and Imaging Agents/Dyes

- Carrier Agents or Buffer Solutions for Injection with any of the above Fluids

FIG. 2

METHOD AND APPARATUS FOR DELIVERY OF GENES, ENZYMES AND BIOLOGICAL AGENTS TO TISSUE CELLS

RELATED CASES

This application is a Continuation-in-Part of U.S. patent application Ser. No. 09/105,896 filed Jun. 26, 1998, now U.S. Pat. No. 6,231,591.

BACKGROUND OF THE INVENTION

1. Field of the Invention

The present invention relates generally to methods and apparatus for injecting treatment fluid into a body, and more particularly to a method for interstitially injecting treatment fluid including genes, enzymes, biological agents, etc., using a needle, guided to a target tissue of any body organ through use of minimally invasive endoscopic instruments or non-invasive imaging techniques.

2. Brief Description of the Prior Art

A variety of treatment fluids are currently known to be of benefit in treating illness in particular body parts. For example, there are a number of tumor suppressor genes, viral vectors, markers, vaccines, enzymes, proteins and biological agents that can be used for gene therapy and cancer treatment. The current method of delivery of these substances is to inject them into the blood stream through use of a conventional needle and syringe. The result is that the substance is carried by the blood to every part of the body. In many cases, it would be advantageous to be able to treat only a particular organ, or part of an organ.

Laparoscopic/endoscopic surgical instruments exist that allow a surgeon to see inside the body cavity of a patient without the necessity of large incisions. This reduces the chances of infection and other complications related to large incisions. The endoscope further allows the surgeon to manipulate microsurgical instruments without impeding the surgeon's view of the area under consideration. Although endoscopic surgical instruments are well developed and in use for surgical operations, an apparatus and method is not described or used in the prior art for delivering a treatment fluid interstitially to a precise target area within a body.

It is therefore apparent that there is a need for a method and apparatus that can deliver a treatment fluid to an interior localized body area.

SUMMARY OF THE INVENTION

It is therefore an object of the present invention to provide a method of injecting a specific treatment fluid to a localized interior body part.

It is another object of the present invention to provide a method of injecting treatment fluid to a localized body portion through use of an endoscopic surgical instrument.

It is a further object of the present invention to provide a method of injecting treatment fluid to a localized body portion by guiding a needle through the body to the localized portion by use of a non-invasive imaging device.

It is a still further object of the present invention to provide an apparatus for injecting treatment fluid to a target area in a body.

It is another object of the present invention to provide an apparatus for directing a needle tip to a target area in a body.

It is a further object of the present invention to provide an apparatus for non-invasive observation of needle position for guiding the needle to a target area, and for monitoring injection of treatment fluid.

Briefly, a preferred embodiment of the present invention includes a method and apparatus wherein treatment fluids, including genes, enzymes and biological agents, are injected into a target area of a body providing selective attachment to the specific target cells without affecting normal tissue cells. The method is used to treat prostate cancer, breast cancer, uterine cancer, bladder cancer, stomach, lung, colon, and brain cancer, etc. A hollow core needle is inserted into a body, the needle being visually guided by a selected imaging technique. A first embodiment utilizes an endoscopic instrument, wherein a probe is inserted into the body, guided by the endoscope to the vicinity of the target area. The hollow core needle is guided to the vicinity by a channel through the probe. A needle adjustment apparatus is used to extend or retract the needle and adjust needle tip orientation toward a target area. The endoscope provides a view to an operator for adjustment of the apparatus to extend the tip of the needle into and through tissue, interstitially, to a target area for deposit of the specific treatment fluid. A non-invasive imaging technique is used either alone, or in addition to the endoscope, to give an operator a view of the needle for guiding the needle tip to the precise target. area. Typical non-invasive techniques include CT scan, MRI, ultrasound, etc.

An advantage of the present invention is that it allows a lethal fluid to be injected into a tumor without seriously affecting the surrounding healthy tissue.

A further advantage of the present invention is that it provides a selective treatment of cancer cells, avoiding the need to inject toxic substances throughout a patient's body.

BRIEF DESCRIPTION OF THE DRAWINGS

FIG. 2 is a listing of preferred treatment fluids;

DETAILED DESCRIPTION OF THE PREFERRED EMBODIMENTS

Figure 1:
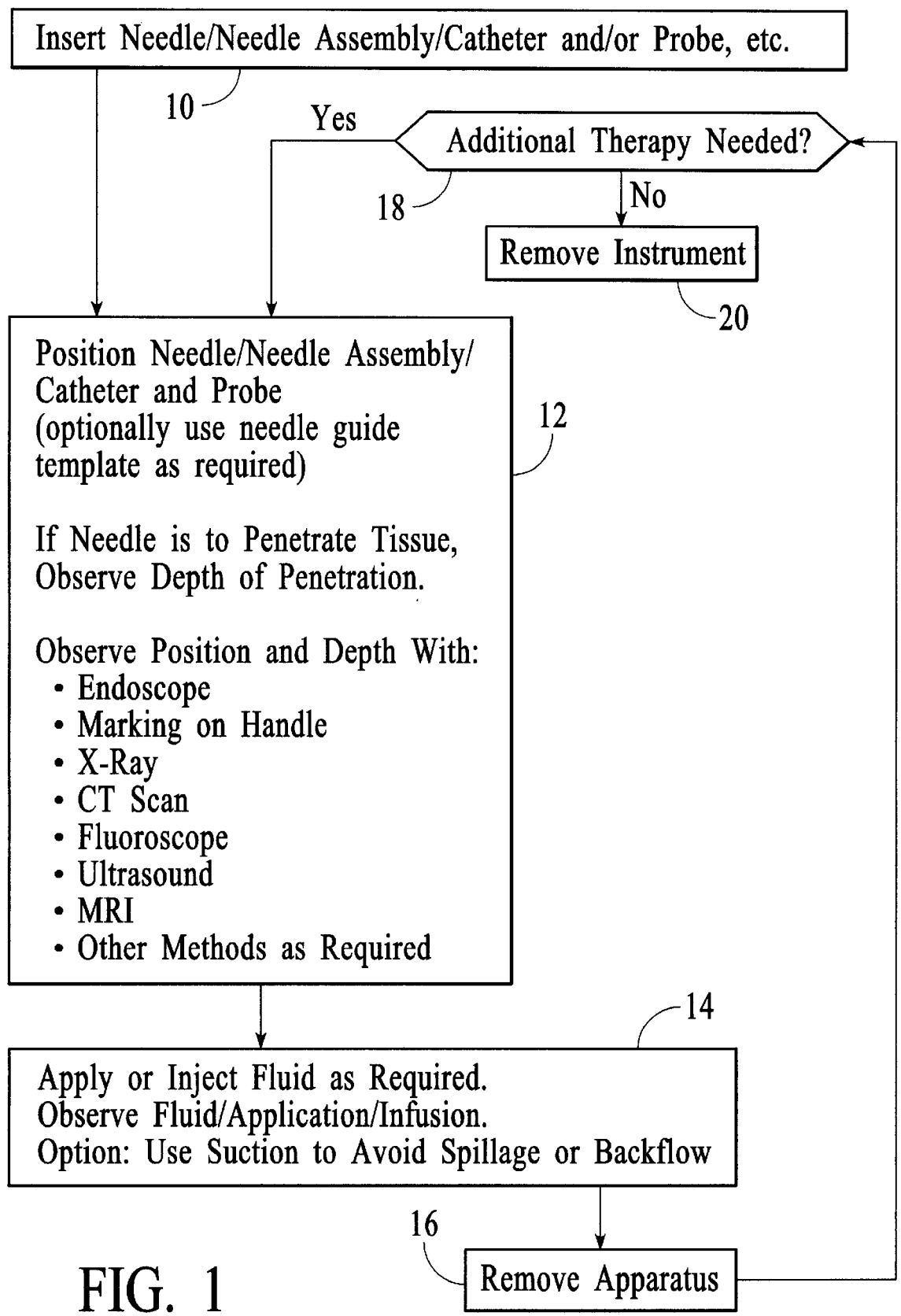
FIG. 1 is a flow diagram showing a preferred embodiment of the method of the present invention.

The preferred embodiment of the present invention will now be described in reference to the flow chart of FIG. 1. A hollow core needle, or probe and hollow core needle or catheter is/are inserted into a patient's body (block 10) through an appropriate opening, such as an incision, or through a natural passageway such as a urethra or cervical canal, etc. If a catheter or probe is used, the hollow core needle can be inserted through the probe or catheter either before or after insertion of the probe or catheter in the body. Through use of an endoscope, and/or a non-invasive detection positioning and imaging method, for example using ultrasound, etc., the user accurately positions the needle near a site to be treated (block 12). Having arrived near the target area, either an endoscope and/or non-invasive detection and imaging methods such as X-RAY, CT SCAN, MRI, ultrasound, fluoroscopy, etc. can be used to guide the needle or an appropriate needle assembly to a target area to be treated, and to monitor injection of treatment fluid. The needle assembly can be solely for application or injection of fluid to a precise target tissue location, or it can be additionally for application of RF energy.

According to the method of the present invention, the needle is used either to apply fluid to a tissue surface, or is advanced interstitially into body tissue in need of treatment (block 12), the needle depth being observed by use of any of various methods, such as those listed including an endoscope for viewing marks on the needle, etc., a scale on the injector or probe handle, or noninvasive imaging and position detection using X-RAY, CT scan, fluoroscopy, ultrasound etc.

For the purpose of the present disclosure, a non-invasive imaging technique is defined as any technique that allows observation of tissue or structure such as a needle in tissue without the use of additional invasive equipment for providing a view using visual light, such as the use of an endoscope or actual cutting away of tissue for a direct view. An ultrasound probe, for example, could be inserted by any means, through a natural opening, or through an incision to a point of interest, and then could provide a non-invasive view of an area beyond the probe through use of ultrasound imaging equipment. This use will be termed non-invasive and referred to in the following disclosure.

The preferred embodiment of the invention includes an apparatus and method for directing a needle to a target area by bending the needle. This is particularly useful in the application wherein a flexible needle assembly is passed inside a catheter through a urethra to the vicinity of a prostate. A needle guiding apparatus is then used to deflect the needle tip toward the specific target area in the prostate. This will be described in full detail in the following disclosure.

With the needle tip at the target. tissue, treatment fluid is injected (block 14) into the specific target tissue without affecting the surrounding area. The needle is then removed from the treatment site (block 16).

At this point the apparatus can be either removed, or a new site in need of treatment can be identified and therapy applied. The process of identification is indicated by block 18. In the case where an endoscope is used, with or without the aid of observation with X-RAY, CT scan, fluoroscopy or ultrasound, the probe can be moved to observe additional tissue to determine further areas in need of treatment. If observation is limited to X-RAY, CT scan, fluoroscopy, ultrasound, these tools are used alone to determine any additional targeted treatment areas. In either of the tool combinations noted above, they are used to precisely locate the targeted treatment area, place and/or insert the needle to the desired depth, and observe the fluid flow and effect on the tissue. If no further treatment is required, the probe, needle assembly, and endoscope (if present) are removed (block 20). If further treatment is required, the probe and needle are positioned accordingly (block 12) and the needle is used to apply fluid to the tissue surface, or it is advanced into the tissue, and a sufficient volume of fluid is injected (block 14).

The present invention provides the method and apparatus for application of fluid to a localized targeted interior tissue surface, or to a similar localized targeted volume of tissue by injection. This is a significant advantage over prior art methods wherein fluid injection affects larger areas including the whole body.

According to the method of the present invention, the fluid can be of any kind for any purpose. A summary of preferred fluids is included in FIG. 2. A preferred embodiment includes the use of a necrossing agent for causing a localized death of tissue. Fluids that can be used for the purpose are listed, and include ethanol alcohol (1% to 100%), saline solution (0.9% to 99%), acetic acid (1% to 100%), and natural extracts. In this case where the fluid is for the purpose of causing tissue death, the fluid is applied/injected at a rate to cause the tissue death in a localized targeted area without affecting surrounding tissue.

The necrossing agent can be combined with carrier agents and/or an anesthetic agent and/or with an antibiotic. Anesthetic agents, for example, include Lidocaine, Markaine and Sensorcaine as listed in FIG. 2, and other anesthetic agents known by those skilled in the art. Similarly, antibiotic agents include the various products known in the art. The method of the present invention also has a significant advantage in gene therapy. The prior art method of gene delivery injects genes into the body intravenously or into-arterially using a conventional needle. This distributes the genes throughout the body. Ideally, the genes should be confined to the target area. Genes are listed in FIG. 2, as are other substances that for many illnesses, such as the treatment of tumors, should optimally be injected directly into the tumor or other target tissue. These include viruses, vaccines, proteins, tumor suppression genes, inhibitors, markers, and other biological agents. The fluids that can be used in accordance with the therapy of the present invention also include mixtures. of the above listed items and other chemicals, agents and their solutions in the form of liquid, gel, suspensions or semi-liquids that will be understood by those skilled in the art.

The method of FIG. 1 according to the present invention is meant to cover treatment of any body part. Preferred embodiments of the present invention include treatment of the prostate, uterine myoma, fibroids, liver ovarian cancer, bladder cancer, breast tumors and cysts (benign or malignant), and stomach, lung, colon and brain cancer, etc., and in the procedure of endometrial ablation of the uterine lining. An important embodiment in use with male patients is treatment of BPH (benign Prostatic Hyperplenia), enlarged prostate growth and prostate cancer. In this case, the probe is typically inserted transurethrally (through the male urethra) or transperineally with or without an incision.

Figure 3:
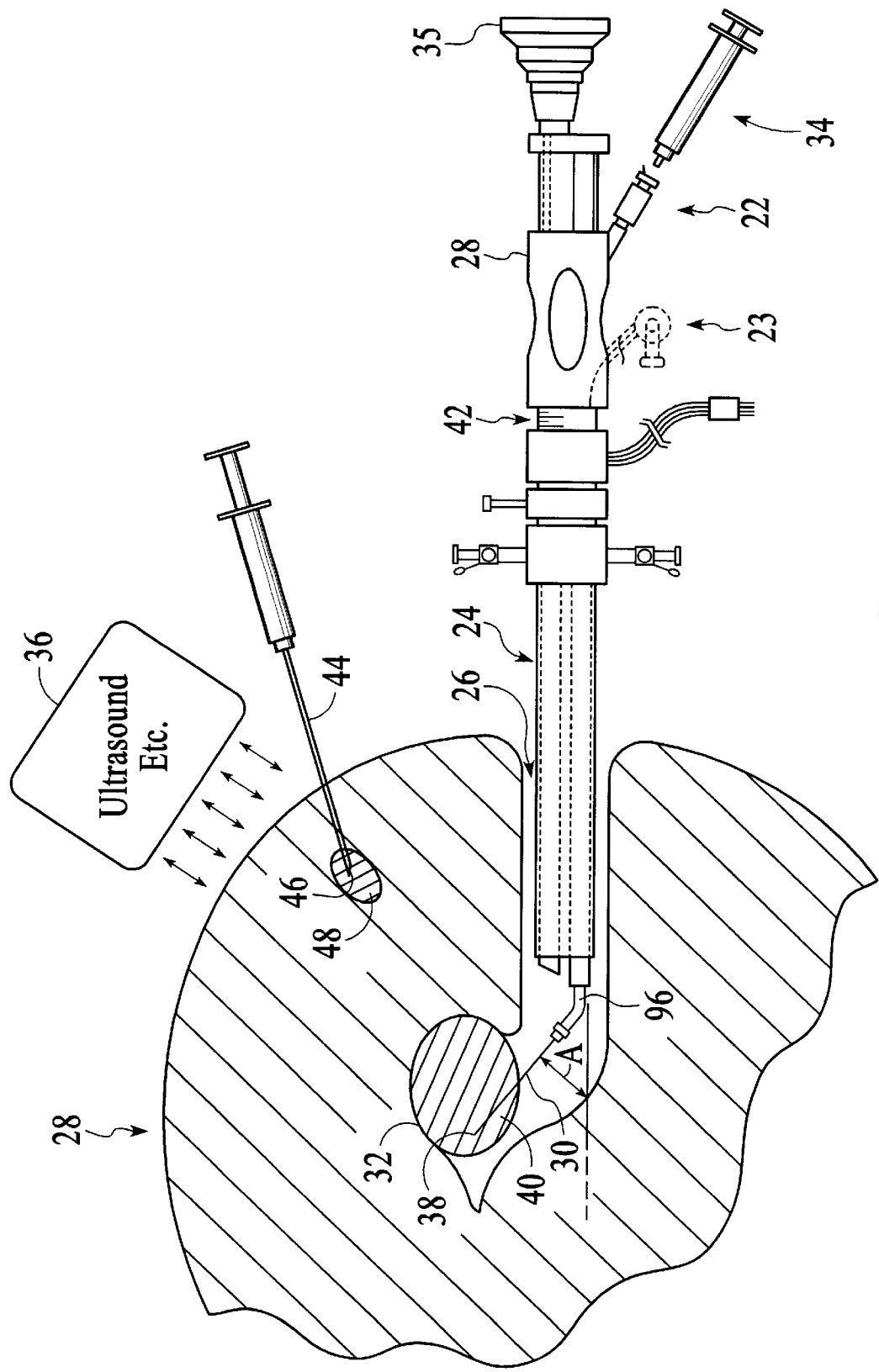
FIG. 3 illustrates use of an endoscope and non-invasive technique for guiding a needle.

The apparatus for guiding the needle according to the present invention includes the apparatus disclosed in copending U.S. patent application Ser. No. 09/105,896 filed Jun. 26, 1998, and is incorporated within the disclosure of the present invention by reference. The endoscope described in detail in reference to FIG. 25 in Ser. No. 09/105,896 is shown in FIG. 3 of the present invention as endoscopic apparatus 22. The probe 24 is shown inserted in an opening 26 of a body 28. A hollow core needle 30 is shown extended by a slidable portion 28 of instrument 22 and directed at an appropriate angle "A" by apparatus 23, etc., so as to cause the needle 30 to be inserted, interstitially, into a tumor 32. A syringe 34 can then be activated to cause a selected treatment fluid to be ejected at the target area, which in this case is in the tumor 32. The probe and needle can be guided within the opening 26 by the scope 35, or optionally the scope 35 can be omitted, and the probe can be guided through use of a non-invasive guidance method, illustrated symbolically as item 36, which can be ultrasound, etc., as listed in FIG. 1.

FIG. 3 also illustrates the use of the non-invasive imaging (ultrasound, etc.) apparatus 36 to guide an operator in positioning needle 44 to a centrally located target area within a tumor 48.

Another non-invasive method, referred to briefly above, is the use of an ultrasonic probe. In this case, the probe can be included inside the hollow core of the needle with the probe tip containing an emitter and detector of ultrasound. This will be more fully explained in reference to the following figures of the drawing. The needle can also be enclosed in a sheath with a bellows and wire apparatus, described fully in U.S. patent application Ser. No. 09/105,896, and also described in further detail in reference to the following figures of the drawing. The bellows and wire or other apparatus such as a pre-tensioned needle in a sheath, as described in U.S. patent application Ser. No. 09/105,896, can be used to direct the needle toward the target area.

The needle depth of penetration into the tumor 32 can also be monitored through first using the endoscope to place the tip 38 at the edge 40 of the tumor, and then observing a graded scale 42 as the apparatus 28 moves forward to insert the needle.

Figure 4:
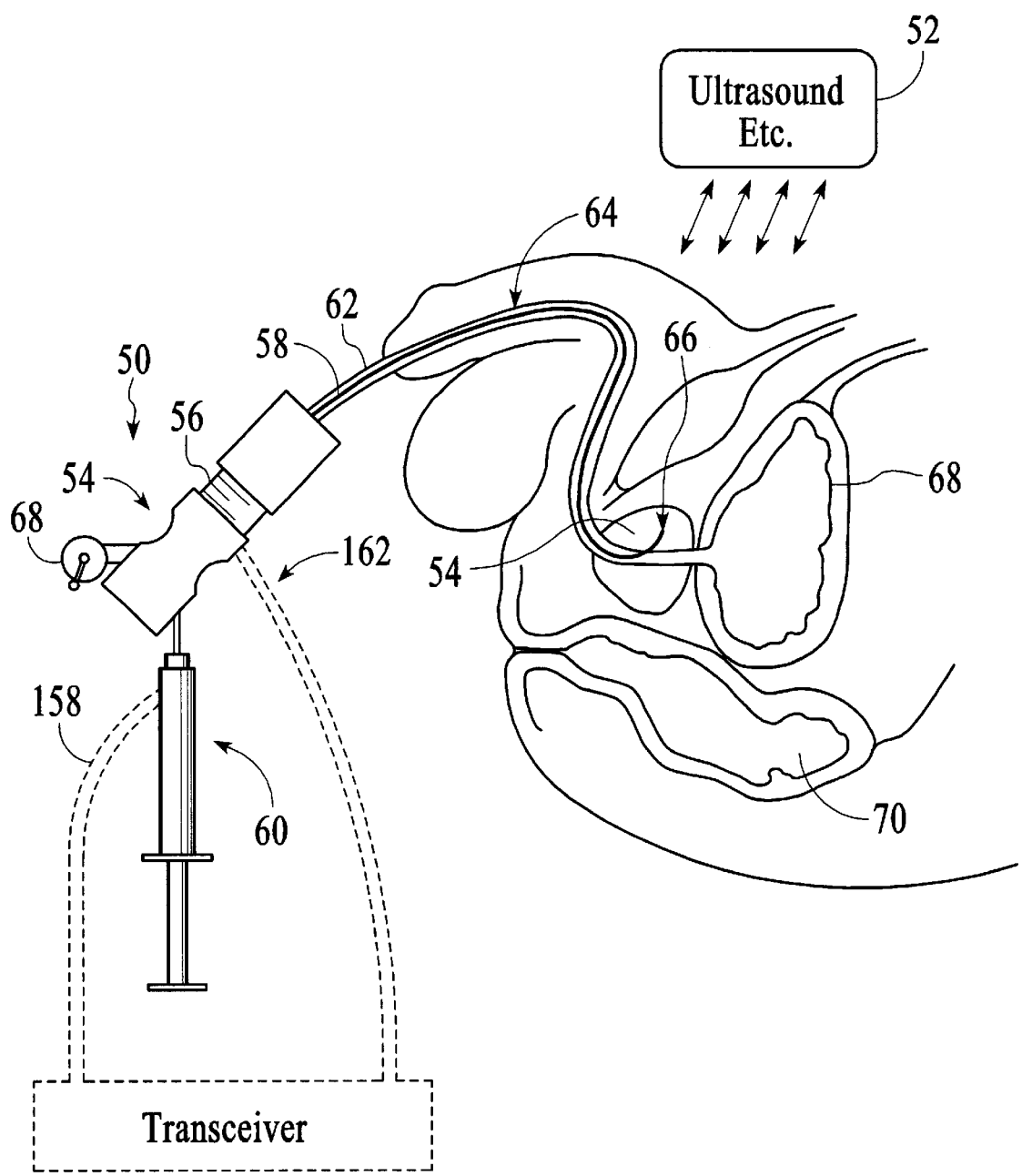
FIG. 4 illustrates use of a flexible probe for traversing a urethra.

FIG. 4 illustrates another embodiment of the present invention wherein an injector apparatus 50 with the aid of a non-invasive imaging device 52, and/or an ultrasonic probe referred to above, is used to inject treatment fluid into a prostate 54. The apparatus 50 includes an adjustable portion 54 with a scale 56 for extending and retracting a flexible hollow core needle 58, constructed in a similar manner to the adjustable portion 28 in FIG. 3 (and FIG. 25 of Ser. No. 09/105,896), including also the syringe apparatus 60 for injection of treatment fluid through the needle 58. The probe 62 in apparatus 50 differs from the probe 24 of FIG. 3. Probe 62 is flexible, allowing some conformance to a urethra 64, or other opening as required. The needle 58 is shown bent upward with the tip 66 positioned in the prostate 54. In order to accomplish the bend in the needle, the needle can either be pre-stressed to direct it at an angle upon leaving the probe 62 as described in detail in Ser. No. 09/105,896, or a bellows and wire apparatus can be used as described in Ser. No. 09/105,896 and described further in the following disclosure. To incorporate the bellows and wire, an extra sheath employing the bellows and wire can be provided inside the catheter through which the needle extends. Alternatively, the sheath can serve as the catheter. As a further alternative, a larger probe such as probe 24 of FIG. 3 can be used to incorporate the apparatus described in reference to FIGS. 24 and 25 of Ser. No. 09/105,896, including the guide wire 293 and sheath 290. The wire tensioning apparatus is described symbolically in FIG. 3 as item 23, and item 68 in FIG. 4.

An alternate embodiment of the method and apparatus for treating the prostate includes the use of a cystoscope (endoscope), such as endoscope 22 of FIG. 1, to place the needle near the prostate, and then to use the pretensioned needle or wire and sheath apparatus to direct the needle at an angle, which is then extended using the apparatus with the depth of penetration through the urethra wall and into the prostate 54 monitored through use of the scale 56 or the non-invasive imaging equipment 52, and/or an ultrasound probe.

FIG. 4 also shows a bladder 68 and rectum 70, as examples of organs that can be reached and treated through use of the method of the present invention.

The method of the present invention is not limited to using the endoscope apparatus discussed herein and in Ser. No. 09/105,896. Any type of scope apparatus that can be used to guide a needle to a target area is applicable to the method, such as cystoscopes, endoscopes, hysteroscopes, laparoscopes, bronchoscopes, gasteroscopes, etc.

Further details of the apparatus for use in the injection of treatment fluid will now be described in reference to FIGS. 5–17. For a more detailed discussion in relation to the apparatus of FIG. 3, refer to Ser. No. 09/105,896.

Figure 5:
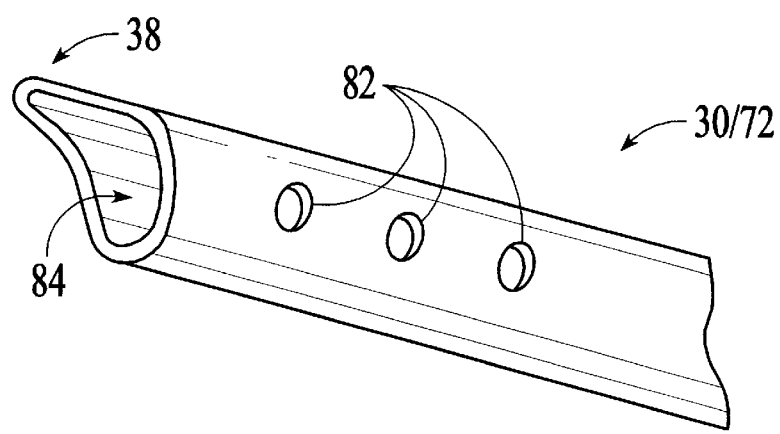
FIG. 5 shows the fluid delivery openings in a sharp or pointed needle.

The tip 38 of the needle, which can be needle 30, as depicted in FIG. 3, can be configured as shown in FIG. 5, with or without holes 82 in the side of the needle 30/72 for dispensing of fluid in addition to hole 84 in the end of the needle. It should be noted that the needle can exit the probe at any angle, and can be either straight or curved. A needle having a portion that curves after exit from the probe or conduit is fabricated by constructing the needle from a resilient material that is pre-stressed in a curved shape, as discussed above in reference to FIGS. 3 and 4. A preferred material is a nickel-titanium alloy. Curved needles of this type are shown as items 86–90 of FIG. 6, illustrating their curved behavior after exiting the probe.

The present invention also includes various combinations of the features of the apparatus as disclosed in FIGS. 25–28 and 30 of Ser. No. 09/105,896 and FIG. 3 of the present invention. For example, although the apparatus includes electrode apparatus, endoscope apparatus, and fluid injection apparatus, the spirit of the invention includes a probe with the fluid injection/application apparatus alone, or with an endoscope and/or with the electrode apparatus or any combinations of these items. For example, if fluid injection/application capability is the only feature needed, the diameter of probe 26 can be significantly reduced, easing entry into the body as illustrated for example in reference to FIG.

4. These and other combinations that will be apparent to those skilled in the art are included in the spirit of the present invention.

Figure 6:
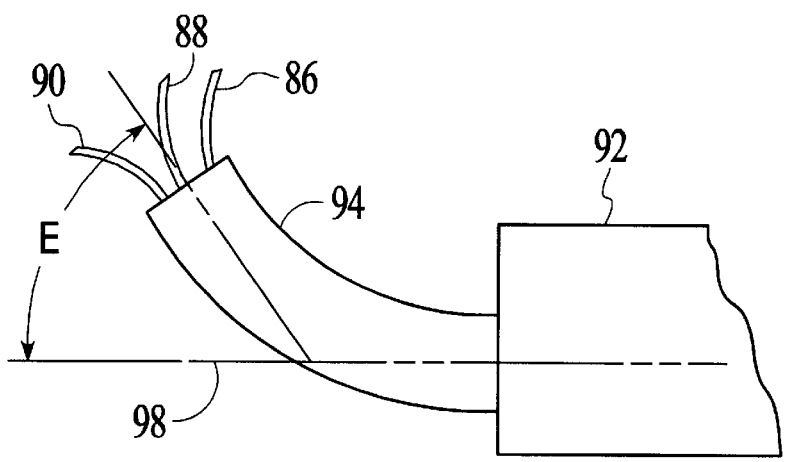
FIG. 6 illustrates multiple needles extending from and at an angle to an axis of a probe.
Figure 7:
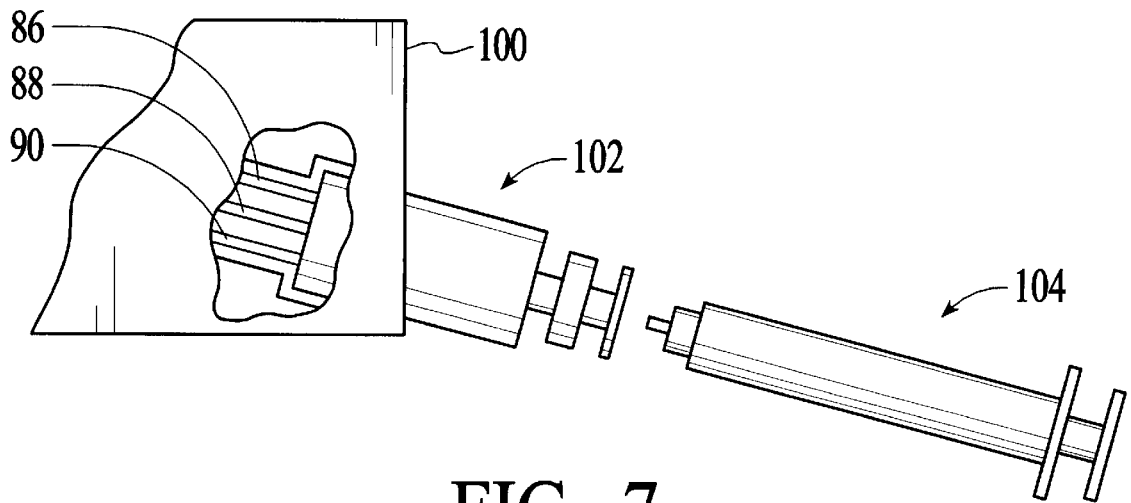
FIG. 7 shows apparatus for injection of fluid into multiple needles.

Referring to FIGS. 6 and 7, the use of multiple hollow core needles 86, 88, 90 is illustrated. FIG. 6 shows a probe 92, similar to probe 24 of FIG. 3 except for having a sleeve 94, similar to sleeve 96 of FIG. 3, except with capacity for the three needles 86, 88 and 90. The needles can exit at any angle "E" relative to the axis 98 of the probe 92, the specific angle "E" dependent on the bend of the sleeve 94. Although FIG. 6 shows three needles, any number of needles are included in the spirit of the invention. The needles 86, 88, 90 are extended and retracted in a similar manner as described above for a single needle. A preferred construction of the needles is from a resilient nickel-titanium alloy, and the needle being pre-stressed into a curved shape. FIG. 7 shows a slidable portion 100, similar to slidable portion 28 of FIG. 3, except configured to accommodate the multiple needles 86, 88, 90. Also shown is an assembly 102 for adapting the needles to a fluid injector 104, similar to injector 34 of FIG. 3.

A still further embodiment of the present invention includes insertion of a needle into a body directly without the use of a probe for guidance as illustrated in FIG. 3, either through a natural opening or through an incision, or by direct insertion using the sharp needle point to puncture/incise the tissue as the needle is inserted. The position of the needle in this case can be guided using ultrasound, MRI, CT scan, etc., as illustrated in FIG. 3. The needle tip is guided to a position adjacent a target tissue surface for topical application of fluid, or is inserted into the target tissue/organ for injection of fluid.

Figure 8:
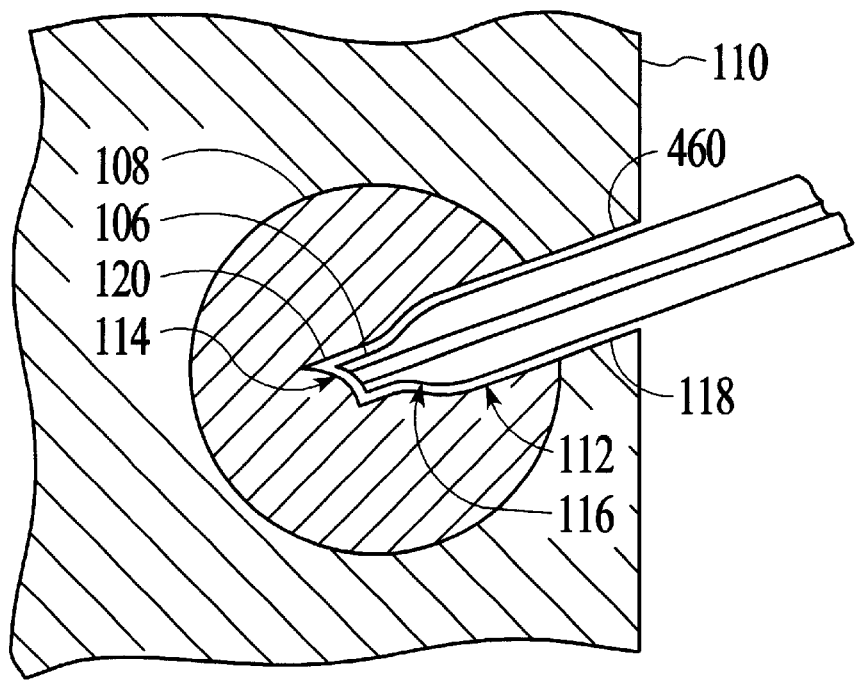
FIG. 8 illustrates use of a needle without a probe for fluid therapy.
Figure 9:
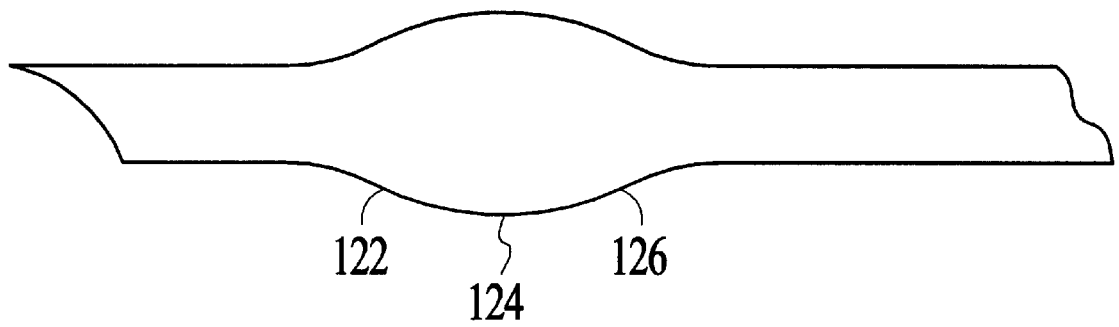
FIG. 9 shows a needle with a fluid block.

FIG. 8 is used to illustrate the insertion of a needle 106 in target tissue 108 inside a body 110 without the guidance of a probe as explained above, and also to illustrate the use of an enlarged section 112 behind a tip 114 of the needle 106. A tapered section 116 permits easier needle entry. The purpose of the enlarged section 112 is to provide a zone of increased contact between the tissue surface 118 in contract with the needle relative to the contact between the needle and tissue surface 120 near the needle tip. The increased contact is a result of the larger expansion of tissue, and the purpose is to provide a barrier to keep fluid exiting at the needle tip 114 from traveling back along the outside of the needle. This feature helps assure that the zone of treatment will be localized to the area immediately surrounding the needle tip. The needle 106 with enlarged region can be used in the embodiments described above in cooperation with a probe, etc. or it can be used by itself as illustrated in FIG. 8. Other ways of constructing a fluid block to keep liquid from traveling back will be apparent to those skilled in the art after reading the disclosure, and these are included in the spirit of the present invention. For example, an abrupt increase in needle diameter in back of the tip will also work, or as shown in FIG. 9, a taper 122 to a short area 124 and then a taper 126 back down again. The enlarged area can also be constructed from a separate, snug fitting sleeve over the needle.

Figure 10:
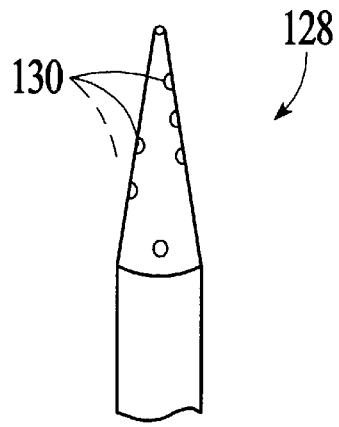
FIG. 10 shows a needle with a conical tip and fluid delivery holes.
Figure 11:
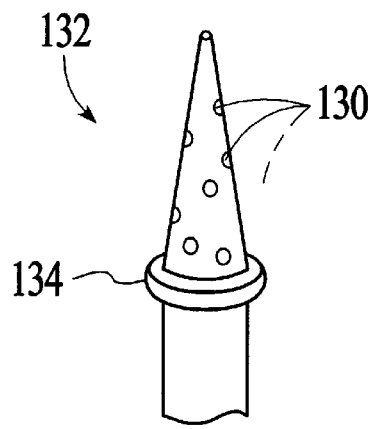
FIG. 11 shows a conical needle tip with a fluid block.
Figure 12:
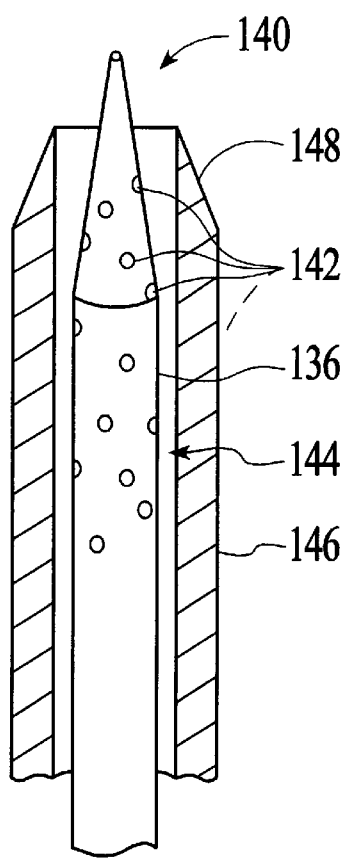
FIG. 12 illustrates a needle core with a plurality of delivery holes selected with a slidable sleeve.
Figure 13:
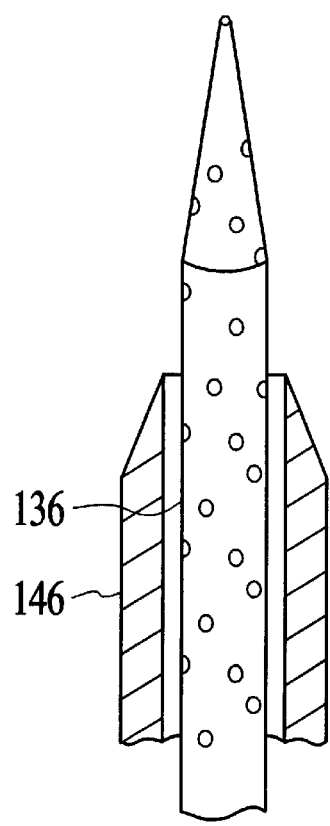
FIG. 13 shows the slidable sleeve in a second position for treating a larger area.

FIG. 10 shows a conically shaped needle tip 128 with fluid delivery holes 130. FIG. 11 shows a conical tip 132 similar to tip 128 but with an enlarged region 134 for blocking fluid. FIGS. 12 and 13 show a needle 136 with a conically tapered tip 140 and delivery holes 142 spaced along the conical tip 140 and a length of the non-conical portion 144. An adjustable sleeve 146 is shown with a tapered end 148 for ease of entry. The sleeve is a close fit over the needle, and is shown in FIG. 13 blocking all of the holes on the straight portion but allowing fluid to escape from the holes 142 in the tapered tip 140 due to the space between the sleeve and the tip. This position provides a minimal zone of fluid treatment. As the sleeve 146 is moved back, the zone of treatment is increased, as shown in FIG. 13. The needle assembly of FIGS. 12, 13 can be used alone with a fluid injector, similar to the illustration of FIG. 8, or with the apparatus as shown in FIG. 3 or other compatible apparatus.

A preferred embodiment of the present invention utilizes what will be referred to as a transurethral and/or interstitial ultrasound imaging method and apparatus for guiding the needle and monitoring the distribution of treatment fluid. The term "transurethral" in this case refers to passing an ultrasonic 41 probe through the urethra, and the term "interstitial" refers to passing the probe into tissue by puncturing, in this case with the needle used to transfer the treatment fluid. The term "imaging" refers to the display of an image on a screen. In the preferred embodiment, ultrasound is used to provide image signals for generation of image data for viewing the tissue to be treated and for monitoring the flow of treatment fluid. The method can be used to treat any body part, through any passage, as through tissue. The application of the method to the urethra will be described in reference to FIG. 4.

Figure 14:
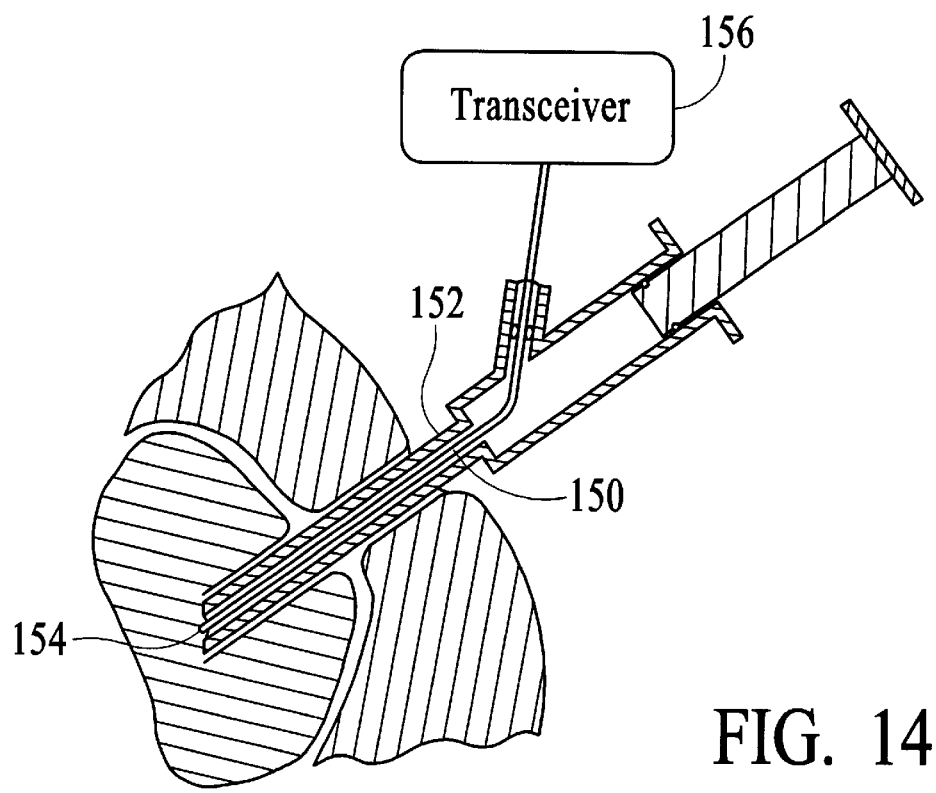
FIG. 14 illustrates use of an ultrasound probe with a hollow core needle.

The method using ultrasound to guide placement of the needle and to observe the injection of treatment fluid is illustrated in an embodiment in FIG. 14. The method is similar to that illustrated in FIG. 3 in reference to needle 44, the method using an external ultrasonic device 36, except that FIG. 14 shows an ultrasonic probe 150 inserted through a needle 152. The probe 150 contains an ultrasonic emitter and an ultrasonic collector embedded near the distal end 154, and transmission lines interconnecting the emitter and collector with the ultrasonic transceiver 156. For the purpose of the present disclosure, the transceiver 156 includes the necessary elements for visual display of the image. The construction and operation of ultrasonic probes, transmitter, receiver or equivalent transceiver and displays are well understood by those skilled in the art and need not be described in detail herein in order for such a person skilled in the art to reproduce the invention.

As a further embodiment, a flexible ultrasonic probe is included inside a catheter, such as catheter 62, or inside the needle 58 or the device shown in FIG. 4. For inclusion inside the needle 58, the probe can access the needle as indicated in FIG. 4 by dashed lines 158, entering injector 60 from the side. A detected ultrasound signal line and a signal transmission line are symbolically represented by the lines also leading to an ultrasonic transceiver 160. In the case where the probe is carried alongside the needle 58 in the catheter 62, the probe can be inserted separately, as at 162 alongside injector 60 for example.

Figure 15A:
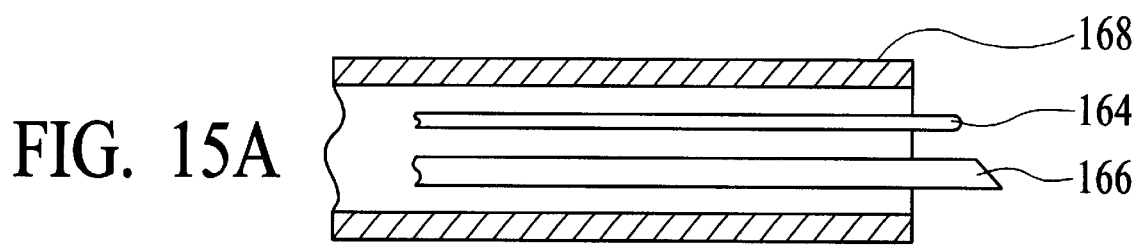
FIG. 15a illustrates an ultrasound probe alongside a hollow core needle inside a catheter.
Figure 15B:
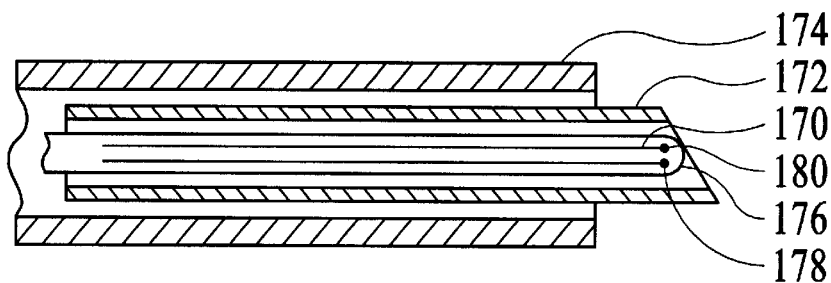
FIG. 15b illustrates an ultrasound probe inside a hollow core needle inside a catheter.
Figure 15C:
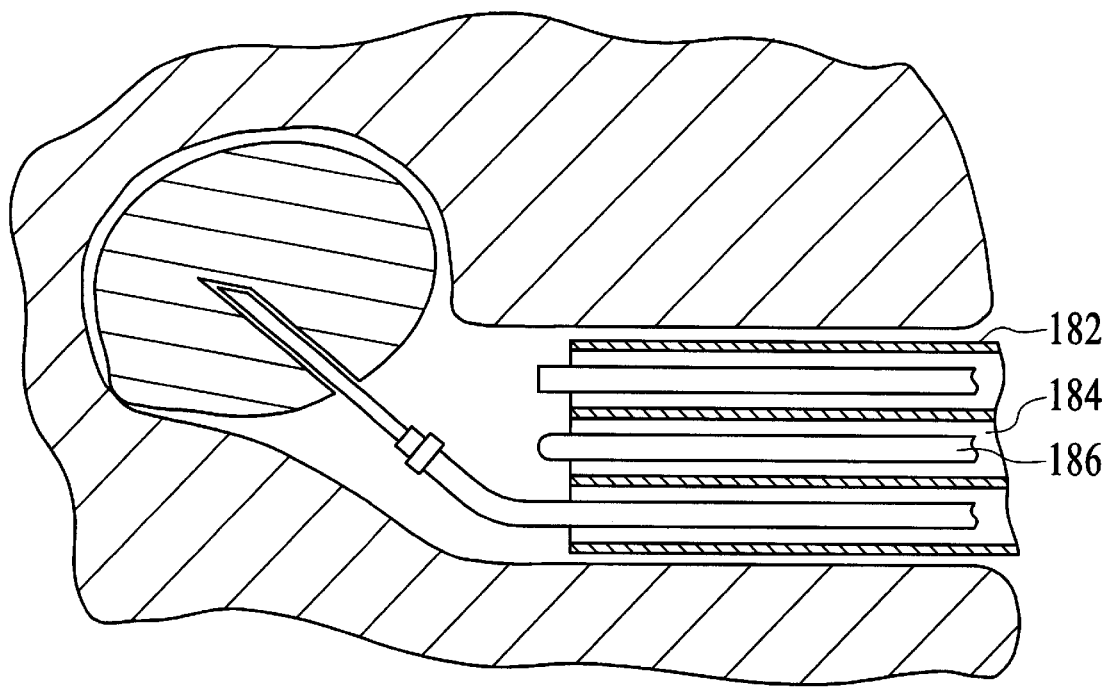
FIG. 15c shows an endoscope probe with an ultrasound probe for non-invasive viewing of interstitial penetration of a needle to a target area.

FIG. 15a illustrates a probe 164 alongside a needle 166 in a catheter 168. FIG. 15b illustrates a probe 170 inside a needle 172, in a catheter 174. Referring to FIG. 15c, a partial view of a probe 182 of an endoscopic instrument is shown. The endoscopic instrument can be similar to the one shown in FIG. 3, except for an additional lumen/channel 184 for passage of an ultrasonic probe 186 for providing a view for guiding the probe 182 and needle assembly 184 (similar to that shown in FIG. 3). The needle, probe and catheter arrangements of FIGS. 15a and 15b can be used with the apparatus 50 illustrated in FIG. 4, and with the endoscope apparatus 22 of FIG. 3. In the case of FIG. 15b where the probe is inside the needle, the probe is preferably held in a fixed position relative to the needle so that the probe distal end 176 (FIG. 15) is always at the distal end of the needle. In operation with the configuration of FIG. 15b, the probe ultrasonic sensor 178 and emitter 180 symbolically illustrated in FIG. 15b are in a position to provide data to the transceiver to display the required area in the vicinity of the needle tip for use in guiding the needle to a target tissue and/or monitoring the injection of treatment fluid.

Figure 16:
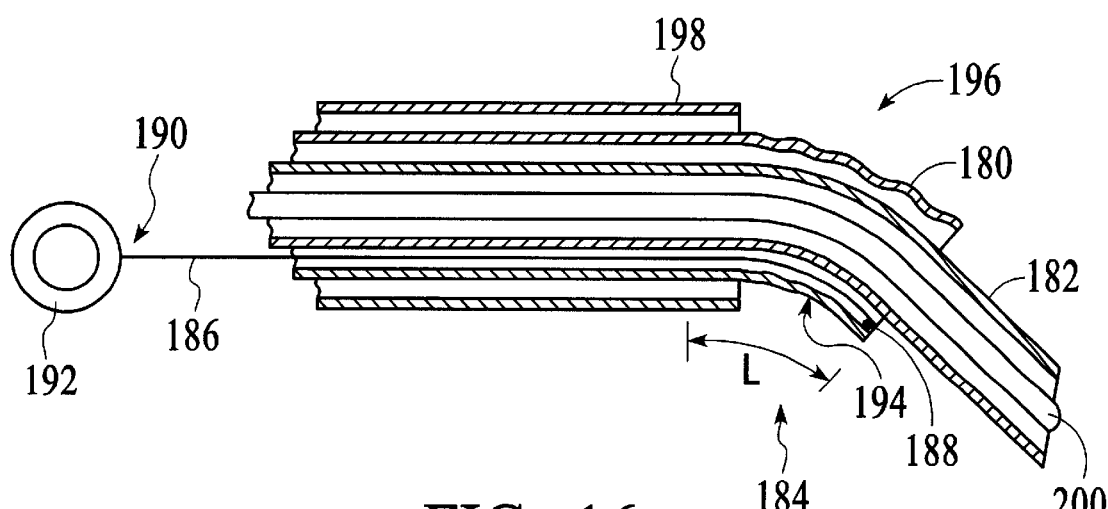
FIG. 16 illustrates use of a wire and bellows construction to provide for deflection of a needle, as applied to the devices and methods of FIGS. 14–15c.

FIG. 16 illustrates the use of a bellows and wire mechanism that is used for bending the needle an/or probe as required to direct the needle to a target area. A detailed description of this type of wire and bellows mechanism is described in Ser. No. 09/105,896 incorporated in the present disclosure by reference. In summary, a sheath 180 is used to guide a flexible hollow core needle 182. The sheath 180 is constructed to be flexible in a lateral direction to its axis, but generally rigid axially except over a length L at the sheath distal end 184. The sheath is preferably constructed in a bellows configuration over the length L, allowing collapse in an axial direction under compression. A wire 186 positioned inside the sheath is attached at the sheath distal end as indicated at 188 by any of various methods known to those skilled in the art. The proximal end 190 of the wire 186 is attached to any of various types of devices indicated symbolically by ring 192 for use by an operator in retracting the wire, which causes the area at 194 over length L to collapse on the side of the sheath to which the wire is attached. This causes the opposite side 196 to bend as shown in FIG. 16, deflecting the needle 182 as required. FIG. 16 also shows the sheath enclosed inside a flexible catheter 198 and an ultrasonic probe 200 inside the needle 182. FIG. 4 is an illustrative example of the use of the construction of FIG. 16 for passing a needle through the urethra 64 and then deflecting the needle toward the prostate, allowing it to enter the prostate interstitially to a target area, along with the ultrasonic probe 200 in the alternate embodiment described above in reference to FIG. 4. The knob 68 is representative of a mechanism for tensioning and retracting the wire 186 to deflect the needle. The wire and bellows mechanism was also referred to briefly in reference to FIG. 3 in use with an endoscope 35 and rigid probe 24. The sheath 96 and needle 30 can be replaced with an assembly as shown in FIG. 16 with the wire retracting device indicated in FIG. 3 as item 23, as discussed above. The present invention also includes the construction wherein the sheath 180 serves as a catheter, or i.e. the catheter serves as the sheath, eliminating the need for the catheter 198 of FIG. 16.

Figures 17, 18:
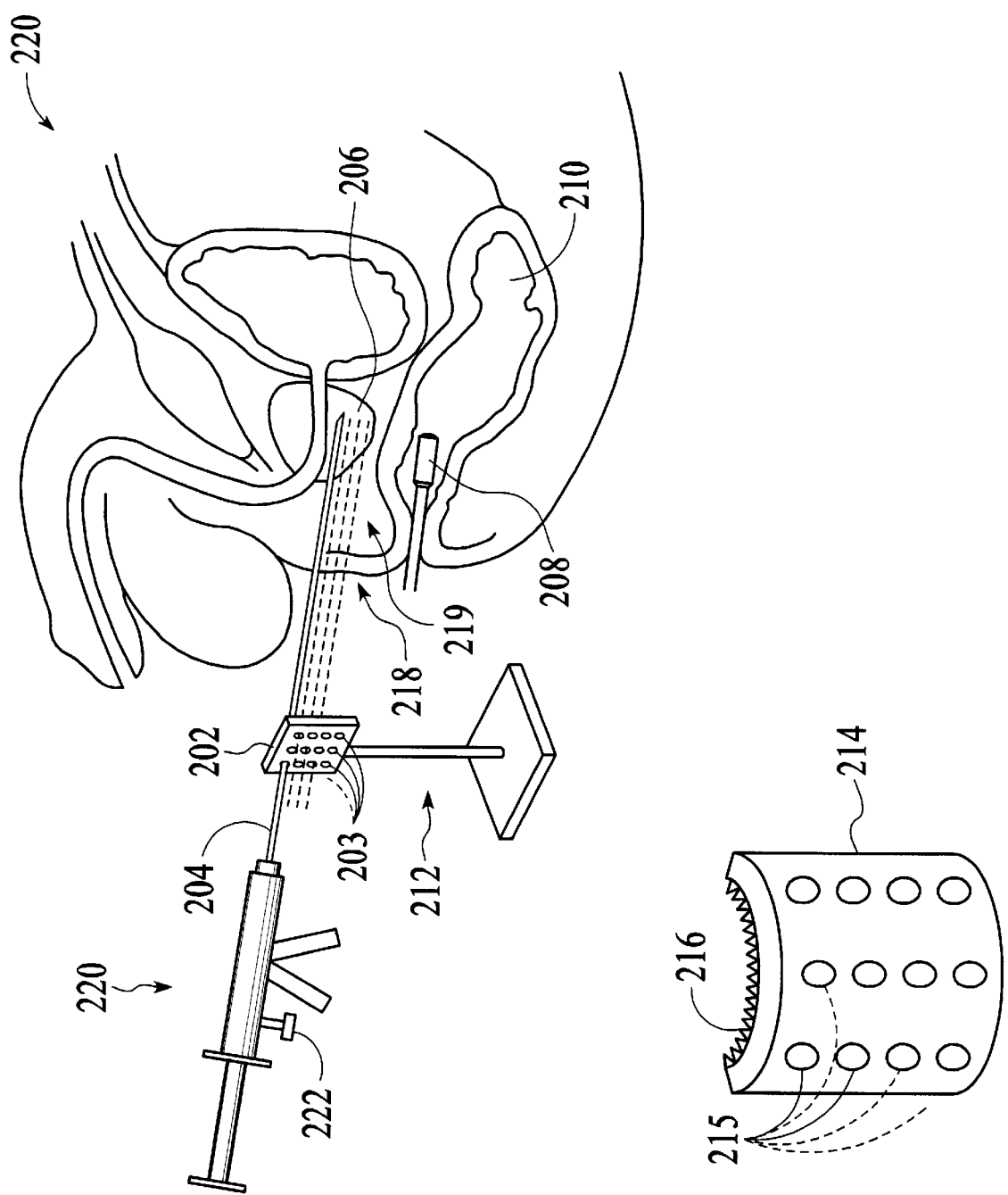
FIG. 17 illustrates the use of a guide template for directing a needle.
FIG. 18 shows a flexible guide template.

Another embodiment of the present invention is illustrated in FIG. 17. According to the method, a template 202 is provided with a plurality of holes 203 used to guide the placement of a hollow core needle 204. to various points in an internal organ, such as a prostate 206. The template 202 allows the operator to methodically and uniformly inject treatment fluid over a required area of an organ. In order to methodically and uniformly treat a given volume of an organ, the depth of the needle 204 must also be controlled. The preferred embodiment provides position observation through use of an ultrasound device, such as described above in reference to FIG. 3. This can also be done through the use of a scale on the needle 204, or with other direct measurement methods. An example of the use of ultrasound is shown in FIG. 17, wherein a probe 208 is inserted in the rectum 210 to apply ultrasound for use in viewing of the needle 204 as it is percutaneously inserted through the perineum 219 and into the prostate 206. In FIG. 17, the template 202 is shown mounted on a stand 212. An alternate template 214 design with needle guidance holes 215 is illustrated in FIG. 18 constructed of flexible material that can be secured with an adhesive 216 to the body exterior, such as at exterior 218 of the perineum 219 in FIG. 17. The benefit of this arrangement is that the body 220 does not have to be held as rigidly as would be the case with the stand 212 in order to assure maximum accuracy of relative needle placement.

Referring again to FIG. 17, a hand piece 220 is provided to propel a treatment fluid through the needle 204. The hand piece 220 can also have an evacuation port 222 for connection to a vacuum/suction pump for extraction/aspiration of fluid from the body 220.

Figure 19A:
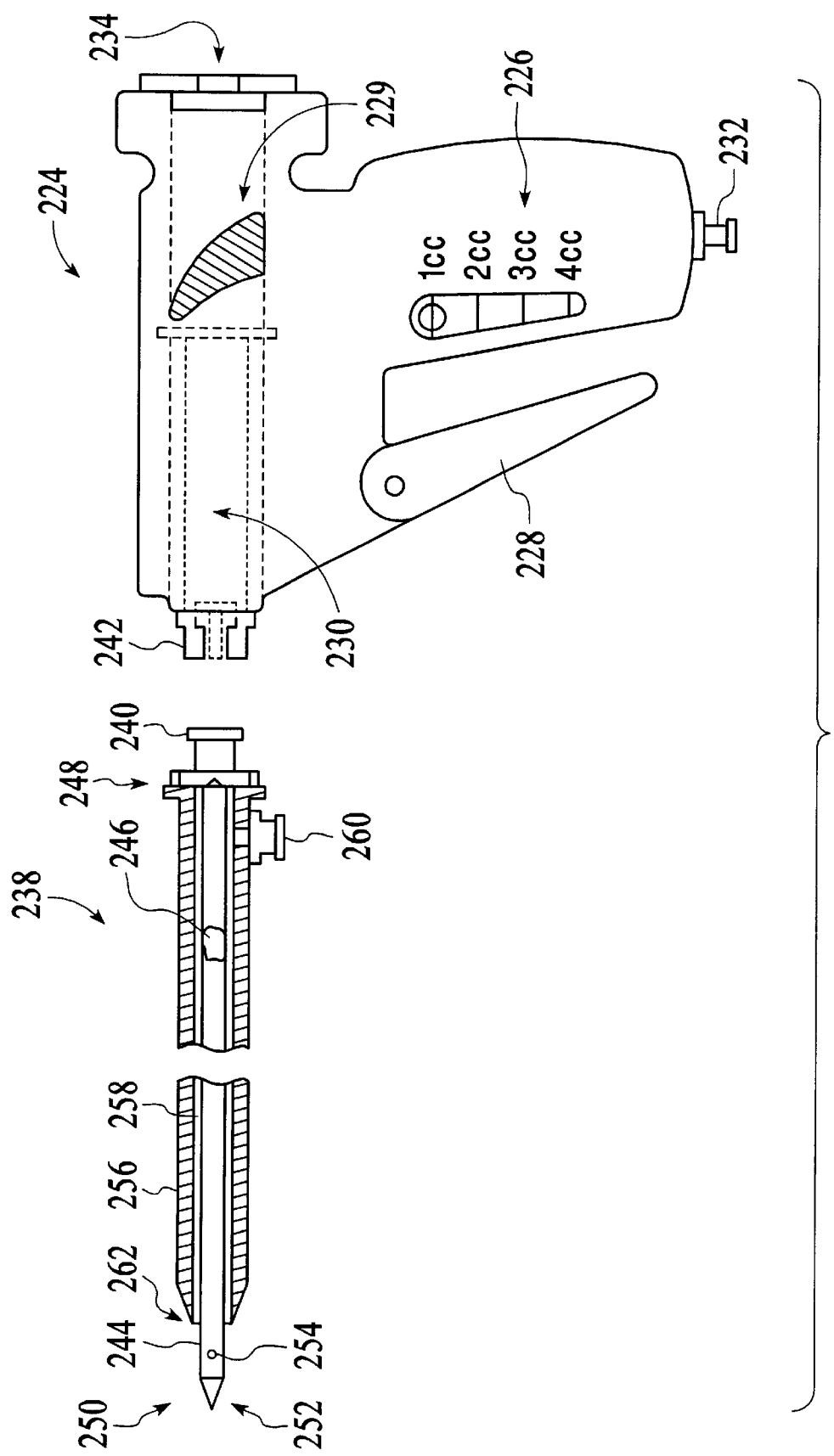
FIG. 19a illustrates a hand piece with evacuation port and adjustable volume dispensing.

Additional and/or alternate features of the needle and hand piece according to the present invention are illustrated in FIGS. 19a–21. FIG. 19a shows a hand piece 224 that can be set to expel a selected measured quantity of treatment fluid through a needle. A fluid quantity/volume selector is indicated at 226. In operation, a trigger 228 is activated to rotate lever 229 to propel the selected volume of fluid from a syringe 230 installed in the hand piece 224. The hand piece is also configured with a canal for evacuation of fluid through a port 232 which in operation is connected a vacuum/suction device.

A needle assembly 238 has an input connector 240 for attachment to a mating connector 242 on the hand piece 224. The assembly 238 has a hollow core needle 244 with a lumen 246 in fluid connection with the connector 240 at a proximal end 248. At a distal end 250, the needle 244 is shown having a tip with a closed point 252. With this needle design, treatment fluid is forced to exit by way of a hole 254 in the side of the needle. Other needle tip designs and exit openings known to those skilled in the art are also included in the spirit of the present invention. The needle 244 is surrounded by an outer sheath 256, shown in a cross-sectional view to illustrate more clearly a gap 258 between the needle and the inner diameter of the sheath. The gap 258 is provided as a canal for the purpose of fluid evacuation by way of a port 260 when attached to a suction/vacuum pump (not shown). The purpose of the sheath and evacuation port 260 is to provide a suction at the end 262 of the sheath to collect treatment fluid exiting the needle that flows back to that point, thereby preventing treatment fluid from traveling away from the desired localized point of treatment in the immediate area of the needle tip, by pulling it through the gap 58 and out port 260.

Figure 20:
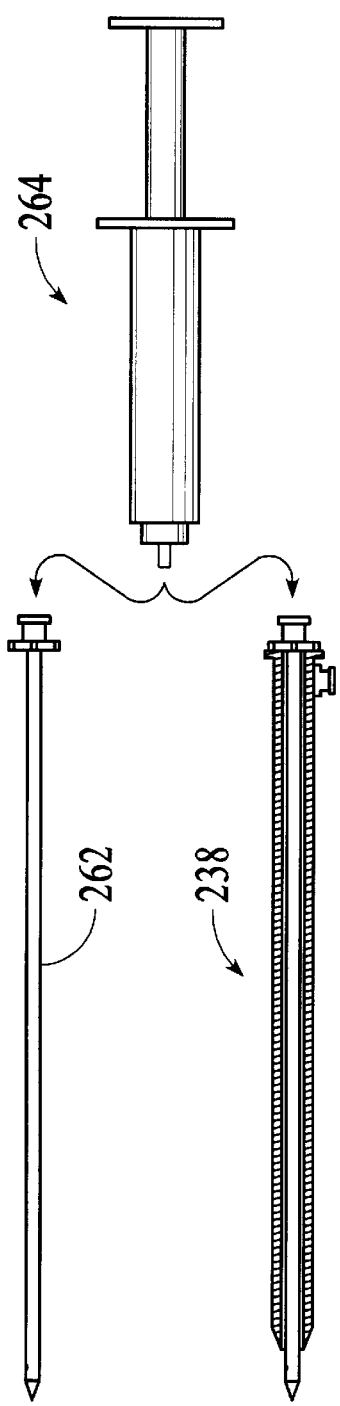
FIG. 20 shows two types of needle apparatus for use with a syringe.

The hand piece apparatus. 224 can be used with either the assembly 238 of FIG. 19a, or with an unsheathed needle such as needle 262 of FIG. 20. The present invention also includes the use of other hand pieces, such as injector apparatus 264 of FIG. 20.

Figure 19B:
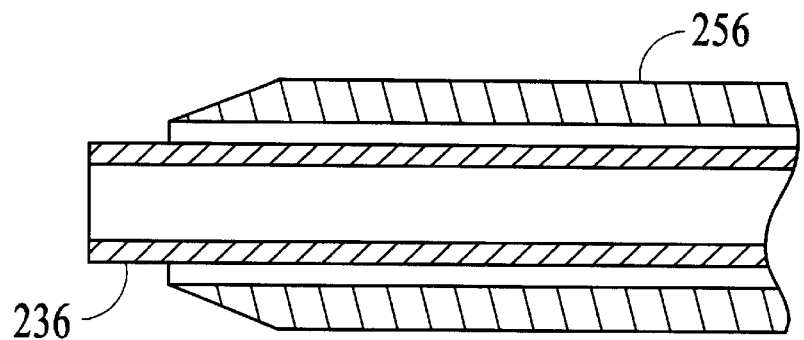
FIG. 19b is a cross-sectional view showing a needle sheath and evacuation port.

The hand piece 224 also has an instrument and image device port 234 through which an instrument or image device can be inserted after removal of the syringe 230. The instrument or image device is symbolically represented by tube 236 in FIG. 19b, and is passed through the hand piece and through a probe such as 256 with an open end, as shown in FIG. 19b.

Figure 19C:
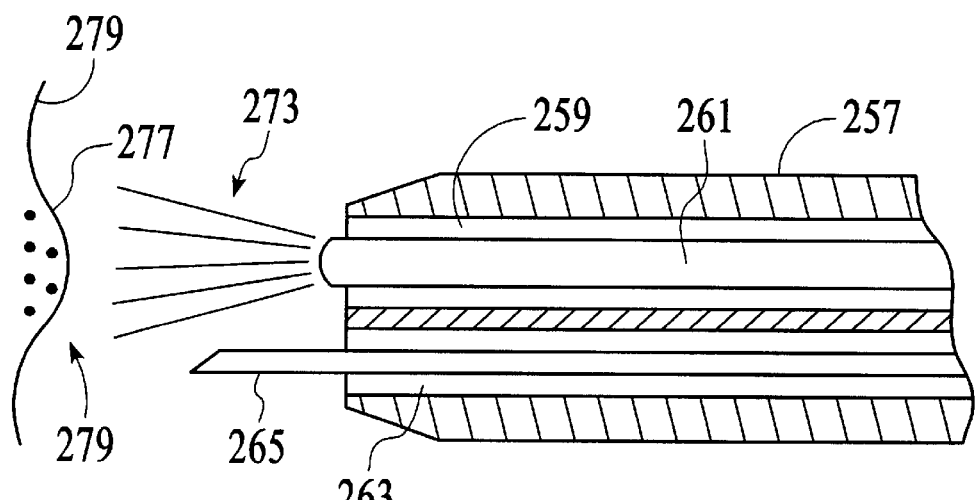
FIG. 19c shows a probe for connection to a handpiece.

FIG. 19c shows a probe 257 that can be connected to a hand piece such as 224 of FIG. 19a, or can be a probe of an instrument such as item 309 shown in FIG. 25 of U.S. patent application Ser. No. 09/105,896 incorporated herein by reference. The probe 257 has a lumen 259 to which an imaging device 261 can be passed, and a lumen 263 for guiding a hollow core needle. 265. The imaging device 261 can be of any type known to those skilled in the art, for example an endascope, or as symbolically illustrated in FIG. 19b as an assembly 267 including an optic fiber 269 for supplying light and a charge coupled device (CCD) 271 for detecting the corresponding light from surrounding tissue.

Figure 19D:
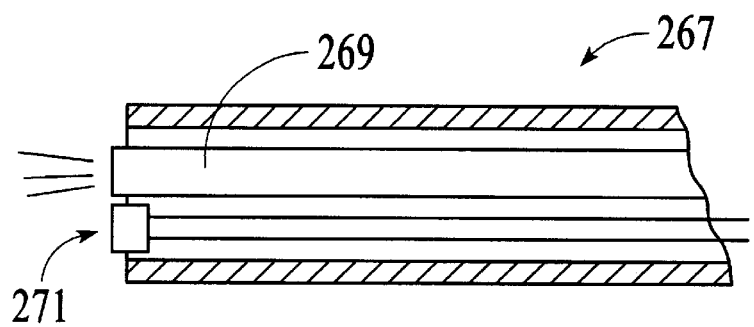
FIG. 19d illustrates a CCD light detection system for use with an endoscope.

According to another embodiment of the present invention, a selected frequency of light 273 is used to illuminate tissue 275. It is known that tumors 277 have a different tissue density and composition than normal cells, and will reflect a different color than healthy tissue 279. Selecting the particular light frequency will therefore make it easier to view the diseased tissue through a color discriminating light detection system such as an endoscope (FIG. 19c) or a properly designed CCD system (FIG. 19d). The present invention also includes injecting tissue with a substance that reflects or emits light, such as a dye or a phosphorescent material that will be absorbed differently by diseased tissue. Diseased tissue can then be detected more easily by observing light reflected or emitted from the tissue.

Another method of the present invention for selectively killing cancer cells includes using a fluid that has the property that it is absorbable by cancer cells or tumor, that is not absorbable by healthy tissue. An example of which a fluid is floricine. This fluid in injected into an area having cancer cells is absorbed by cancer cells, in preference over healthy tissue. The next step of the method includes selectively heating the tissue that has absorbed the fluid. This is accomplished by application of a laser beam, or electromagnetic energy (RF waves, microwaves, etc.), or ultrasound, or an electrical current. The fluid filled cells will draw more current or absorb more radiated energy than the non-filled cells, and as a result will be selectively destroyed.

Figure 21:
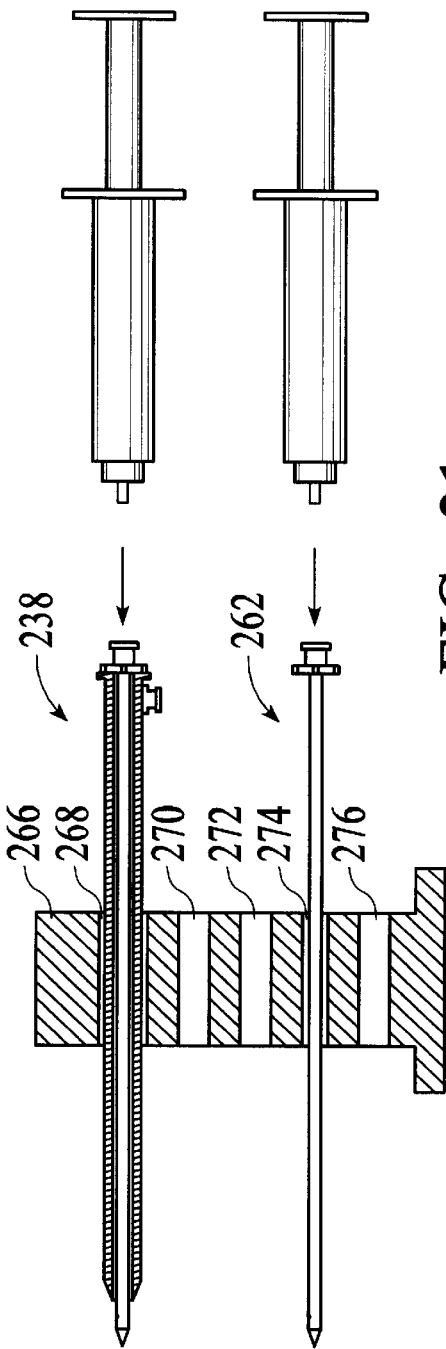
FIG. 21 shows a cross-sectional view of a guide template block.

FIG. 21 shows a cross-sectional view of a guide block 266 with guide holes 268–276 with a needle assembly 238 in hole 268 and a needle 262 in hole 274. In actual use, all of the holes are typically of the same size, and only one needle type is used and inserted in only one hole at a time. Also, in application a hand piece or syringe, such as devices 224 or 264, must be attached to the needle/assembly for injection or evacuation of fluid. Alternatively, a plurality of needles can be inserted through an equal plurality of guide holes, and fluid can be simultaneously propelled through all of the needles, or separately propelled through each needle. FIG. 20 symbolically illustrates connection of a single fluid driver, such as injector apparatus 264, to two needles 262 and 238, for example.

Although the present invention has been described above in terms of a specific embodiment, it is anticipated that alterations and modifications thereof will no doubt become apparent to those skilled in the art. It is therefore intended that the following claims be interpreted as covering all such alterations and modifications as fall within the true spirit and scope of the invention.

I claim:

1. A method for treating a localized portion of body tissue comprising:
   (a) inserting a needle apparatus in a body, said apparatus including at least one hollow core needle for delivering treatment fluid into said body wherein said needle apparatus further includes a sheath having a lumen of greater diameter than an outer diameter of said needle for providing a gap between said needle and said sheath, and said needle extending through said lumen, and said sheath having an evacuation port through a wall of said heath and said evacuation port having fluid communication with a suction connector for connection to a vacuum to extract fluid from said body through said gap;
   (b) guiding said needle apparatus to a target tissue in need of treatment, and said guiding including use of an imaging technique for viewing inside an area of tissue without physically invading said area; and
   (c) applying said treatment fluid to said target tissue through said needle apparatus;
   wherein said treatment fluid is selected from the group consisting of genes, viruses, proteins, inhibitors, tissue markers, bioabsorbable polymers and other biological agents and chemotherapeutic agents.

2. A method for treating a localized portion of body tissue comprising:
   (a) inserting a needle apparatus in a body, said apparatus including at least one hollow core needle for delivering treatment fluid into said body;
   (b) guiding said needle apparatus to a target tissue in need of treatment, and said guiding including use of an imaging technique for viewing inside an area of tissue without physically invading said area wherein said imaging technique is an ultrasound technique, laser imaging or digital imaging technique; and
   (c) applying said treatment fluid to said target tissue through said needle apparatus;
   wherein said treatment fluid is selected from the group consisting of genes, viruses, proteins, inhibitors, tissue markers, bioabsorbable polymers and other biological agents and chemotherapeutic agents.

3. An apparatus for injecting treatment fluid into a body comprising:
   an assembly including
   (a) needle apparatus including a hollow core needle for delivering treatment fluid to a target tissue in a body; and
   (b) guiding apparatus for guiding a tip of said hollow core needle to said target tissue and said guiding apparatus including non-invasive imaging apparatus for viewing inside an area of tissue without physically invading said area with said guiding apparatus, wherein said non-invasive imaging apparatus includes ultrasound apparatus, and digital imaging devices;
   wherein said treatment fluid is selected from the group consisting of genes, viruses, proteins, inhibitors, vaccines, tissue markers, bioabsorbable polymers, chemotherapeutic agents and other biological agents.

4. A treatment apparatus for injecting treatment fluid into a body comprising:
   an assembly including
   (a) needle apparatus including a hollow core needle for delivering treatment fluid to a target tissue in a body wherein said needle apparatus further includes a sheath having a lumen, and said needle extending through said lumen, wherein said lumen is of greater diameter than an outer diameter of said needle providing a space between said needle and said sheath, and said sheath having an evacuation port through a wall of said sheath and said evacuation port having fluid communication with a suction connector; and
   (b) guiding apparatus for guiding a tip of said hollow core needle to said target tissue and said guiding apparatus including non-invasive imagine apparatus for viewing inside an area of tissue without physically invading said area with said guiding apparatus;
   wherein said treatment fluid is selected from the group consisting of genes, viruses, proteins, inhibitors, vaccines, tissue markers, bioabsorbable polymers, chemotherapeutic agents and other biological agents.

5. A treatment apparatus as recited in claim 4 wherein said hollow core needle has a tubular wall with a closed distal end and at least one hole in said wall for discharging said fluid.

6. A method for treating a localized portion of body tissue comprising:

(a) inserting a needle apparatus in a body, said apparatus including at least one hollow core needle for delivering treatment fluid into said body;

(b) guiding said needle apparatus to a target tissue in need of treatment, and said guiding including use of an imaging technique for viewing inside an area of tissue without physically invading said area;

(c) applying said treatment fluid to said target tissue through said needle apparatus; and (d) heating said target tissue for selective tissue destruction;

wherein said treatment fluid is selected from the group consisting of genes, viruses, proteins, inhibitors, tissue markers, bioabsorbable polymers and other biological agents and chemotherapeutic agents.

7. A method as recited in claim 6 wherein said heating is accomplished by subjecting said target tissue to energy supplied by a media selected from the group consisting of laser beams, electromagnetic waves, ultrasound, and electrical current.

8. A method for treating a localized portion of body tissue comprising:

(a) inserting a needle apparatus in a body, said apparatus including at least one hollow core needle for delivering treatment fluid into said body wherein said inserting is further performed using a hand piece attached to said needle apparatus, and said hand piece includes fluid delivery apparatus for delivering said treatment fluid through said needle wherein said handpiece is constructed to allow use of an imaging device;

(b) guiding said needle apparatus to a target tissue in need of treatment, and said guiding including use of an imaging technique for viewing inside an area of tissue without physically invading said area;

(c) applying said treatment fluid to said target tissue through said needle apparatus; and (d) illuminating tissue with a selected light frequency for enhancing the detection of diseased tissue;

wherein said treatment fluid is selected from the group consisting of genes, viruses, proteins, inhibitors, tissue markers, bioabsorbable polymers and other biological agents and chemotherapeutic agents.

9. A method for treating a localized portion of body tissue comprising:

(a) inserting a needle apparatus in a body, said apparatus including at least one hollow core needle for delivering treatment fluid into said body wherein said inserting is further performed using a hand piece attached to said needle apparatus, and said hand piece includes fluid delivery apparatus for delivering said treatment fluid through said needle wherein said handpiece is constructed to allow use of an imaging device;

(b) guiding said needle apparatus to a target tissue in need of treatment, and said guiding including use of an imaging technique for viewing inside an area of tissue without physically invading said area;

(c) applying said treatment fluid to said target tissue through said needle apparatus;

(d) injecting tissue with a light discriminating material; and (e) observing light from said tissue to discern diseased tissue from healthy tissue;

wherein said treatment fluid is selected from the group consisting of genes, viruses, proteins, inhibitors, tissue markers, bioabsorbable polymers and other biological agents and chemotherapeutic agents.

10. A method as recited in claim 9 wherein said material is a dye.

11. A method is recited in claim 9 wherein said material is a phosphorescent material.

12. A method for treating a localized portion of body tissue comprising:

(a) inserting a needle apparatus in a body, said apparatus including at least one hollow core needle for delivering treatment fluid into said body;

(b) guiding said needle apparatus to a target tissue in need of treatment, and said guiding including use of an imaging technique for viewing inside an area of tissue without physically invading said area;

(c) applying said treatment fluid to said target tissue through said needle apparatus;

(d) applying a fluid to an area including said target tissue wherein said fluid is selectively absorbable by said target issue; and (e) applying energy to said area to cause selective heating of said target tissue;

wherein said treatment fluid is selected from the group consisting of genes, viruses, proteins, inhibitors, tissue markers, bioabsorbable polymers and other biological agents and chemotherapeutic agents.

* * * * *